United States Patent [19]

Hotta et al.

[11] 4,024,157
[45] May 17, 1977

[54] FLUORAN COMPOUNDS AND RECORDING SHEET CONTAINING THEM

[75] Inventors: Seiji Hotta, Ibaragi; Yukiaki Ito, Minoo, both of Japan

[73] Assignee: Sumitomo Chemical Company Limited, Osaka, Japan

[22] Filed: Oct. 1, 1974

[21] Appl. No.: 510,916

[30] Foreign Application Priority Data
Oct. 5, 1973   Japan..........................48-112591

[52] U.S. Cl. .............................260/335; 282/27.5; 428/488; 260/326.34; 260/293.58; 260/247.5 H; 260/240 R

[51] Int. Cl.² ..................................... C07D 493/10

[58] Field of Search ............................. 260/335

[56] References Cited

UNITED STATES PATENTS

| | | | |
|---|---|---|---|
| 2,031,023 | 2/1936 | Wyler ................................. | 260/336 |
| 3,864,145 | 2/1975 | Seki et al. ........................... | 117/36.2 |
| 3,947,471 | 3/1976 | Akamatsu et al. .................. | 260/335 |

FOREIGN PATENTS OR APPLICATIONS 7,214,690   5/1973   Netherlands

OTHER PUBLICATIONS

Chemical Abstracts, vol. 79, (1973), abstracting Ger.-Offen. 2,253,161, 43672u.

*Primary Examiner*—Norma S. Milestone
*Attorney, Agent, or Firm*—Stevens, Davis, Miller & Mosher

[57] ABSTRACT

A fluoran compound represented by the formula,

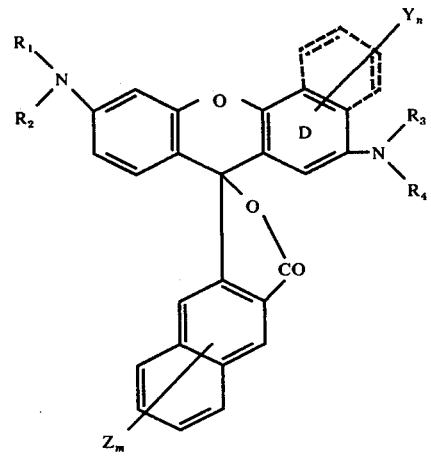

wherein $R_1$, $R_2$, $R_3$ and $R_4$ are each hydrogen, substituted or unsubstituted lower alkyl, lower alkenyl, or lower alkynyl,

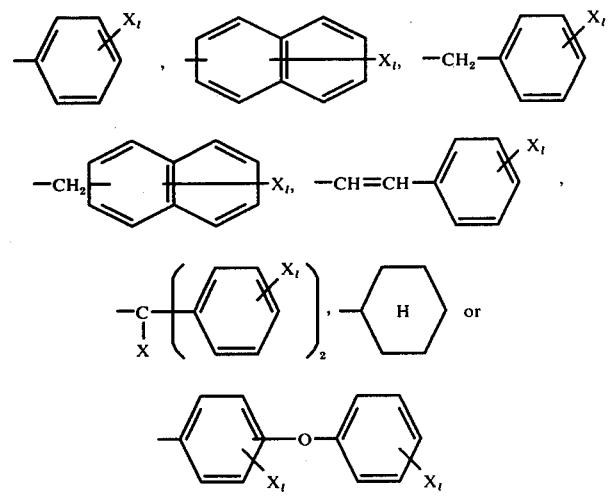

group (wherein X is hydrogen, halogen, lower alkyl, lower alkoxy, di-lower alkylamino or —$COOR_a$ group in which $R_a$ is lower alkyl, and $l$ is an integer of 1 to 4), or $R_1$ and $R_2$, or $R_3$ and $R_4$, taken together, may form a heterocyclic ring; Y is the same atom or group as X but independent of X; D is a benzene or naphthalene nucleus; Z is hydrogen or halogen; and $m$ and $n$ are each an integer of 1 to 4, is useful as a coloring material for record material systems such as pressure-sensitive copying paper or heat-sensitive copying paper, wherein colored images are formed by an electron donor-accepter and color-forming reaction between a coloring material and an acidic material.

3 Claims, 1 Drawing Figure

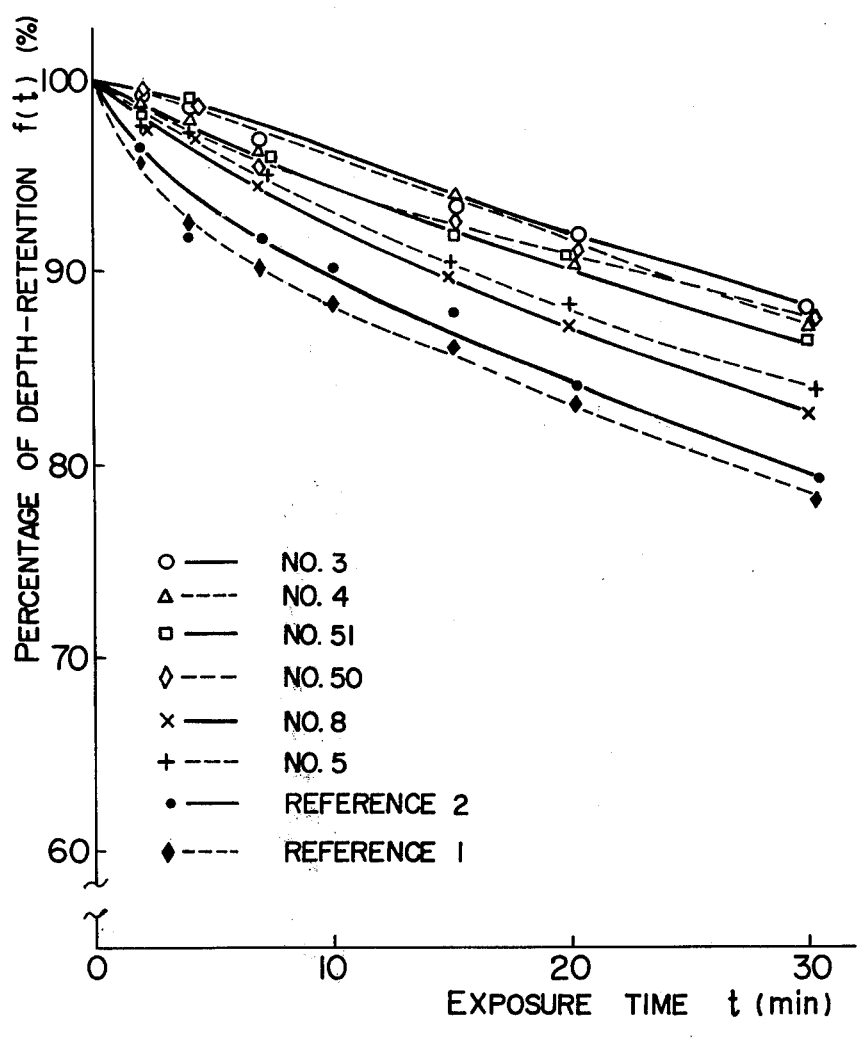

FLUORAN COMPOUNDS AND RECORDING SHEET CONTAINING THEM

This invention relates to chromogenic compounds for use in recording sheets which develop color images by an electron donor-acceptor color-forming reaction between a chromogenic material and an acidic material which react upon contact to produce a color.

More particularly, the present invention relates to novel fluorans represented by the following general formula (I), which have never been disclosed in prior art references, methods for the preparation thereof and recording sheets containing the same as chromogenic materials,

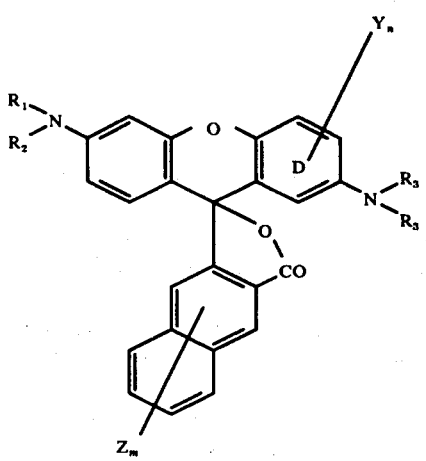

wherein $R_1$, $R_2$, $R_3$ are each hydrogen, substituted or unsubstituted lower alkyl, lower alkenyl, or lower alkynyl,

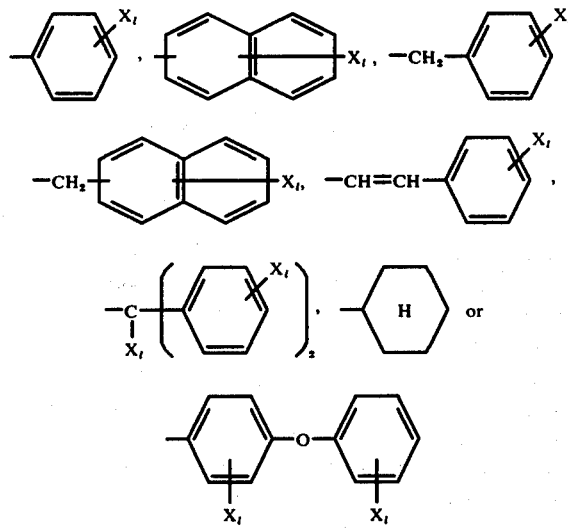

group (wherein X is hydrogen, halogen, lower alkyl, lower alkoxy, di-lower alkylamino or $-COOR_a$ group in which $R_a$ is lower alkyl, and $l$ is an integer of 1 to 4), or $R_1$ and $R_2$, or $R_3$ and $R_4$, taken together, may form a heterocyclic ring; Y is the same atom or group as X but independent of X; D is a benzene or naphthalene nucleus; Z is hydrogen or halogen; and $m$ and $n$ are each in integer of 1 to 4.

Throughout the present specification, the term "lower" as is seen in "lower alkyl" indicates that the number of carbon atoms is 1 to 4.

So far oil carbon paper was used for making out documents and slips as office work materials. It has drawbacks as it is liable to stain clothes and hands and it is troublesome to insert the oil carbon paper between documents and slips.

In order to eliminate the inefficiencies and defects of the oil carbon paper, pressure-sensitive or heat-sensitive copying paper, which is economic and handy, has recently made its debut in place of the oil carbon paper complying with demand for speed-up of office work.

Heretofore, leucoauramines, leucomethylene blues, phthalides and fluorans are well known as color precursors. They are colorless or nearly colorless compounds, which may change to a certain coloring matter when they are brought into contact with an acidic electron-acceptor as explained below.

For example, 2-methyl-6-diethylaminofluoran having the following formula (A) is one of the well-known color precursors which are colorless compounds under ordinary condition but change to red coloring matters by opening their lactone ring when they are brought into contact with an acidic electron-acceptor.

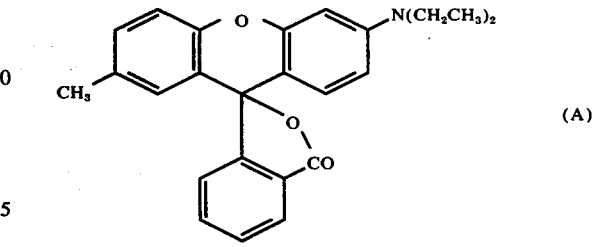

The pressure-sensitive or heat-sensitive copying paper is usually prepared by coating the back side of one sheet of paper with a color precursor such as a leucoauramine or a fluoran, and coating the surface of another sheet of paper with an acidic electron-acceptor such as kaolin, bentonite, activated clay, acid clay, aluminum silicate, attapulgite, metal oxides, metal chlorides, metal sulfates, organic acids such as phenols, aliphatic acids or tannic acid, or phenolic resins such as p-phenylphenol-formaldehyde resin, p-cyclohexylphenolformaldehyde resin, etc. The pressure-sensitive copying paper is used by placing the coating papers upon one another so that the back side of the first paper may be faced to the surface of the second paper, and the back side of the second paper to the surface of the third paper and so on. In case of pressure-sensitive copying paper, by applying pressure or impact to the papers by means of a pencil, a ball-point pen or a typewriter on the first paper, and in case of heat-sensitive copying paper, by heating or infrared heating, the material on the back side and the electron-acceptor substances on the surface of the papers are brought into contact with each other, whereby the colorless pressure-sensitive material moves to the electron-acceptor layer and undergoes color development and therefore colored images can be obtained.

The aforesaid compound (A) has defects that, when used as a color precursor for pressure-sensitive or heat-sensitive copying papers, it stains capsules in undesired red color because it is slightly soluble in water or slightly acidic or alkaline water.

Further, it has a relatively high vapor pressure so that it tends to vaporize from the capsules to form ghost images which contaminate regular images on the pressure-sensitive or heat-sensitive copying paper and to cause the images to disappear on the paper during storage for a long period of time.

The present invention has technical advance over prior arts in the following points:

1. These fluoran compounds represented by the general formula (I) are colorless and stable in air at ordinary temperature, but the compounds (I) change in color from white to red, blue, green, dark green, greenish black and black when they are brought into contact with an acidic electron-acceptor explained in detail above.

2. These fluoran compounds (I) show all sorts of dark colors, for example, dark red, dark green, dark blue-green, dark greenish black, or black according to the number, kind and position of substituents.

These various colors are due to the same fluoran nucleus except the kind, number and position of substituents. The present fluoran compounds have almost the same color developing speed and the pressure-sensitive or heat-sensitive copying paper obtained by mixing the present fluoran compounds shows no lag of the color developing time and changes the color of the image.

It is also possible to use the present compounds together with other color precursors such as C. V. L. (crystal violet lactone), B. L. M. B. (benzoyl leucomethylene blue) or 2-methyl-6-diethylaminofluoran, etc. to obtain a special color such as blue-black or black image on the paper without spoiling the other color precursors. These are significant features of the present invention.

3. The present novel fluoran compounds are well soluble under colorless condition in a non-volatile non-polar solvent used for preparing a recording sheet. Examples of the non-polar solvent are as follows:

Chlorinated benzenes such as trichlorobenzenes and tetrachlorobenzenes; chlorinated biphenyls such as dichlorodiphenyls, trichlorodiphenyls, and tetrachlorodiphenyls; alkylated benzenes; alkylated naphthalenes such as dimethylnaphthalene and dipropylnaphthalene; mineral oil; paraffin oil; olive oil; and tricresyl phosphate, etc.

Good solubility particularly in the aromatic solvents makes it easy to prepare the recording sheet and to obtain a deep image on the paper.

4. The present fluoran compounds have no solubility in water, acids or alkalis and have stability in water, acids or alkalis. For example, they can be boiled with an alkaline solution without being destroyed. Particularly, the present fluoran compounds have good fastness to light.

The obtained deep image on this recording sheet does not disappear or change in color. Furthermore, the obtained image on the recording sheet has good fastnesses to light, heat and water, and it does not disappear or change in color when exposed to light, or brought into contact with water or exposed to high moisture.

The recording sheet prepared with the present fluoran compound endures storage for a long period of time without the disappearance of the image on the documents and slips.

The present fluoran compounds have high color-developing speed. Such color formation occurs just at once when the fluoran compounds in the form of crystals or a solution in the above-cited solvents are brought into contact with the acidic electron-acceptor. Then, the recording sheet prepared with the present fluoran compounds gives vivid deep images on the paper at the moment when a pressure or impact or heat is applied onto the paper by means of a pencil, a ball-point pen, a typewriter, heating or infrared heating.

6. The images on the recording sheet prepared with a mixture of the present fluoran compounds do not change in color owing to the same color-developing speeds caused by the same fluoran nucleus.

7. Some of the present fluoran compounds impart a very deep, pure black image of good performance on the recording sheet prepared with them along as a color-developing material.

The accompanying drawing is a graph showing the light fastness of the fluoran compounds according to the present invention and reference compounds.

The fluoran compounds (I) according to the present invention are prepared by the following two methods.

1. First method m-Aminophenol derivative of the formula (II) is condensed with naphthalene-2,3-dicarboxylic acid anhydride of the formula (III) at 20° to 200° C in an aromatic solvent such as monochlorobenzene, o-dichlorobenzene, trichlorobenzene, nitrobenzene or toluene to obtain 2-(4'-amino-2'-hydroxy)benzoylnaphthalene-3-carboxylic acid derivative represented by the formula (IV). The aforesaid reaction is shown by the following reaction formula,

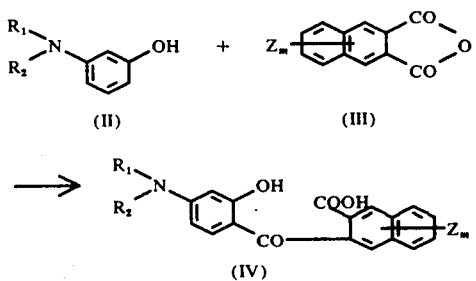

wherein $R_1$, $R_2$, Z and $m$ are as defined above.

Then, the compound (IV) thus obtained is condensed with p-aminophenol derivative of the formula (V) at 0° to 200° C for several to ten-odd hours in the presence of a dehydrating-condensing agent as mentioned below. After completion of the reaction, the reaction solution is poured into ice water and separated precipitates are filtered and neutralized with an alkali to obtain an objective colored product. The reaction is shown by the following formula,

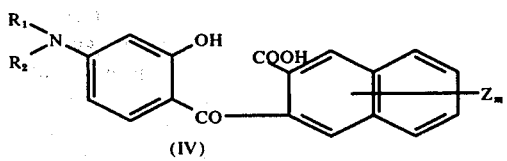

-continued

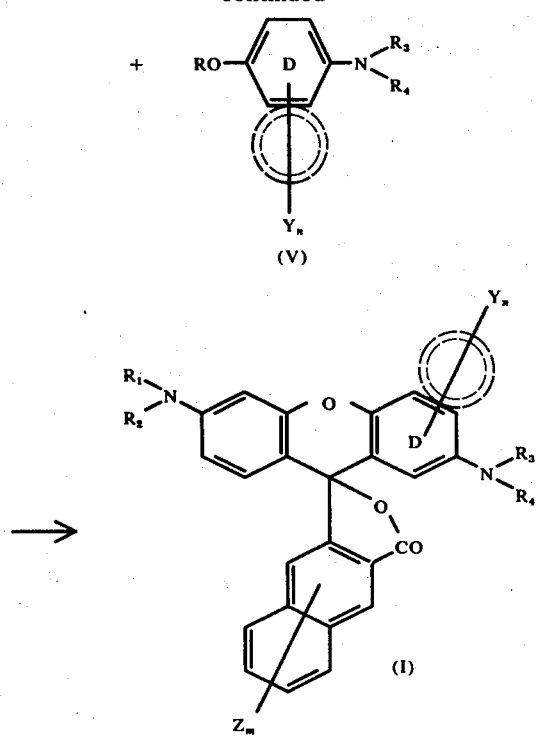

wherein $R_1$, $R_2$, $R_3$, $R_4$, Y, Z, D, m, or n are as defined above, and R is hydrogen, methyl or ethyl.

The resulting colored product is dried, then dissolved in a solvent for recrystallization by heating, (if desired the solution may be concentrated), cooled, filtered and washed with a non-polar solvent, in which the present fluoran compound is hardly soluble, such as cyclohexane, n-hexane and diethylether to obtain a white to faintly colored objective compound (I).

The dehydrating-condensing agents which are used for the reaction include sulfuric acid; phosphorus pentoxide; phosphoric acid; polyphosphoric acid; anhydrous metal halides such as anhydrous tin chloride, anhydrous zinc chloride, anhydrous aluminum chloride and anhydrous ferric chloride; phosphorus trichloride; and phosphorus pentachloride. If necessary, carbon disulfide, chlorinated benzenes or nitrobenzenes are used as a solvent for the reaction.

The solvents used for the recrystallization include aromatic hydrocarbon solvents such as benzene, toluene and xylene, halogenated aromatic hydrocarbon solvents such as chlorobenzene, bromobenzene and dichlorobenzenes, halogenated aliphatic hydrocarbon solvents such as chloroform, bromoform and methylchloroform, and alcohol solvents such as methanol, ethanol, propanol and butanol.

In the method, if it is particularly necessary to carry out formation of a lactone ring, as a solvent for the ring-closure, aromatic hydrocarbons such as benzene and xylene; nuclear halogenated aromatic hydrocarbons such as chlorobenzene, bromobenzene, dichlorobenzenes and trichlorobenzenes; alcohols such as methanol and ethanol; amide solvents such as dimethylformamide and diethylformamide; sulfoxide solvents such as dimethylsulfoxide and diethylsulfoxide; aliphatic hydrocarbons such as n-hexane and cyclohexane; halogenated aliphatic hydrocarbons such as chloroform, bromoform and methylchloroform; and ethers such as dimethylether and diethylether are useful.

The ring formation is often facilitated by the addition of aliphatic amines such as dimethylamine, trimethylamine, diethylamine and triethylamine; aliphatic aminoalcohols such as ethanolamine and propanolamine; and heterocyclic basic substances such as pyridine and picoline.

2. Second method

A diaminofluoran derivative of the formula (I') wherein $R_4$ in the formula (I) is hydrogen is first prepared according to the first method, and then the compound (I') thus obtained is reacted with alkylating agents of the formula (VI) at 30° to 150° C using, if necessary, solvents and acid-binding agents to obtain an objective fluoran compound (I). Treatment after reaction and ring formation are the same as described in the first method.

The reaction is shown by the following formula,

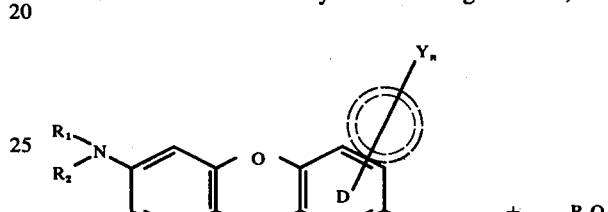

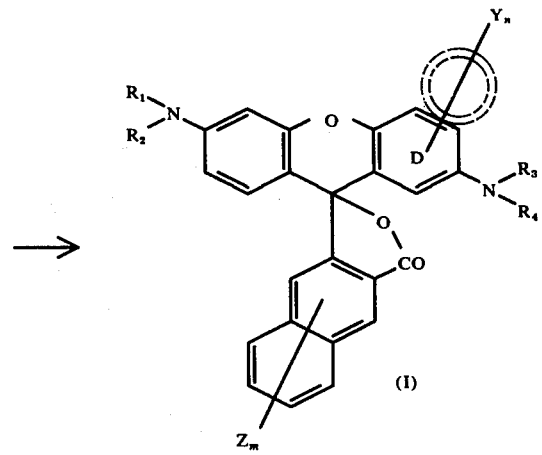

wherein $R_1$, $R_2$, $R_3$, D, Y, Z, m, and n are as defined above, $R_4$ is the same as defined above provided that the case where $R_4$ is hydrogen is excluded, and Q is a residue of the alkylating agent.

Examples of the alkylating agents are as follows:
1. Esters
Dimethyl sulfate
Diethyl sulfate
Dipropyl sulfate
Dibutyl sulfate
Trimethylphosphoric acid
Triethylphosphoric acid Tripropylphosphoric acid
Methyl benzenesulfonate
Ethyl benzenesulfonate
Propyl benzenesulfonate
Methyl p-toluenesulfonate
Ethyl p-toluenesulfonate
Propyl p-toluenesulfonate
Methoxyethyl p-toluenesulfonate
Ethoxyethyl p-toluenesulfonate
Methyl methanesulfonate
Propyl methanesulfonate
2. Lower aliphatic alkyl halides
Methyl chloride
Methyl bromide
Ethyl chloride
Ethyl bromide
Propyl chloride
Propyl bromide
Butyl chloride Butyl bromide
(3) Benzyl halides
Benzyl chloride
p-Chlorobenzyl chloride
o-Chlorobenzyl chloride
p-Bromobenzyl chloride
m-Bromobenzyl chloride
p-Methylbenzyl chloride
o-Methylbenzyl chloride
p-Methoxybenzyl chloride
m-Methoxybenzyl chloride
o-Methoxybenzyl chloride
Benzyl bromide
p-Chlorobenzyl bromide
o-Chlorobenzyl bromide
p-Bromobenzyl bromide
m-Bromobenzyl bromide
p-Methylbenzyl bromide
m-Methylbenzyl bromide
o-Methylbenzyl bromide
m-Methoxybenzyl bromide
o-Methoxybenzyl bromide
1-Chloromethylnaphthalene
2-Chloromethylnaphthalene
Cinnamoyl chloride
Cinnamoyl bromide Examples of the acid-binding agents are as follows:
Sodium hydrogencarbonate
Potassium hydrogencarbonate
Sodium carbonate
Potassium carbonate
Sodium acetate
Potassium acetate
Caustic soda If circumstances permit, the aliphatic amines or aminoalcohols or heterocyclic basic substances mentioned hereinbefore may be used in place of the acid binding agents for promoting a ring-closure.

Examples of the solvent for the alkylation are aromatic hydrocarbons such as benzene and xylene; halogenated aliphatic hydrocarbons such as chloroform, bromoform and methylchloroform; halogenated aromatic hydrocarbons such as chlorobenzene, bromobenzene and dichlorobenzenes; alcohols such as methanol, ethanol and propanol; ethers such as diethyl ether, dimethylene glycol dimethyl ether and diethylene glycol dimethyl ether; sulfoxide solvents such as dimethylsulfoxide and diethylsulfoxide; and amide solvents such as N,N-dimethylformamide, N,N-diethylformamide, dimethylacetamide and N-methylpyrrolidone.

The fluoran compounds of formula (I) which are prepared aaccording to the above-mentioned methods are concretely summarized in the following Table, together with their chemical formulas and colors which are developed on silica gel when their toluene solutions are added dropwise thereon. The colors which are developed on paper coated with acid clay, that is, front paper, are omitted because they are almost the same as those on silica gel.

| Compound No. | Chemical formula | Shade on silica gel |
|---|---|---|
| 1 | (structure) | Black brown |
| 2 | (structure) | Greenish black |

-continued

| Compound No. | Chemical formula | Shade on silica gel |
|---|---|---|
| 3 | | Greenish black |
| 4 | | Greenish black |
| 5 | | Greenish black |
| 6 | | Black brown |

-continued
| Compound No. | Chemical formula | Shade on silica gel |
|---|---|---|
| 7 | 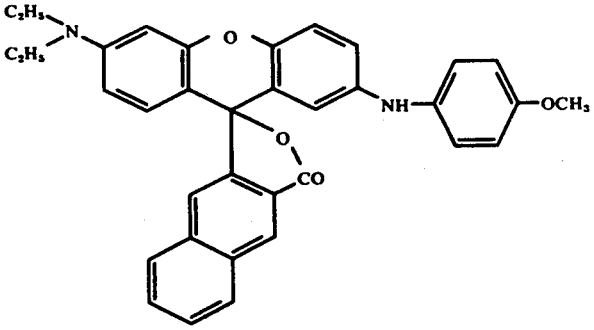 | Green |
| 8 | 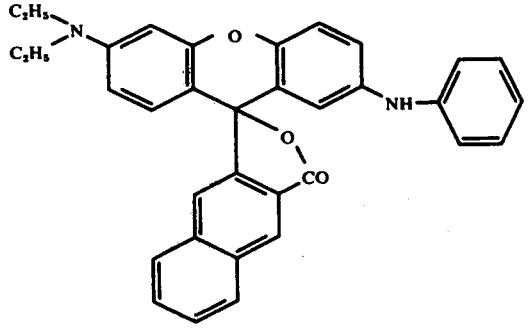 | Black brown |
| 9 | 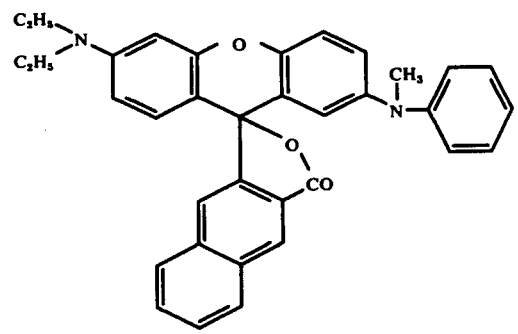 | Black brown |
| 10 | 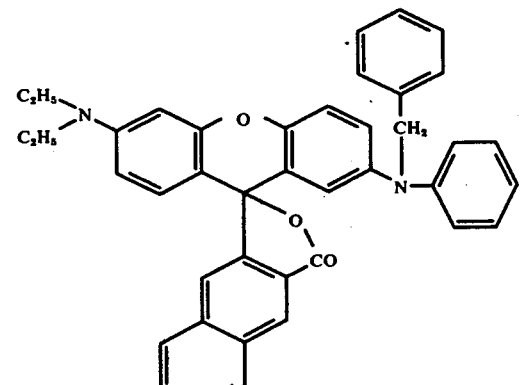 | Dark greenish black |

-continued

| Compound No. | Chemical formula | Shade on silica gel |
|---|---|---|
| 11 | | Black |
| 12 | | Reddish black |
| 13 | | Reddish black |
| 14 | | Reddish black |

-continued
| Compound No. | Chemical formula | Shade on silica gel |
|---|---|---|
| 15 | 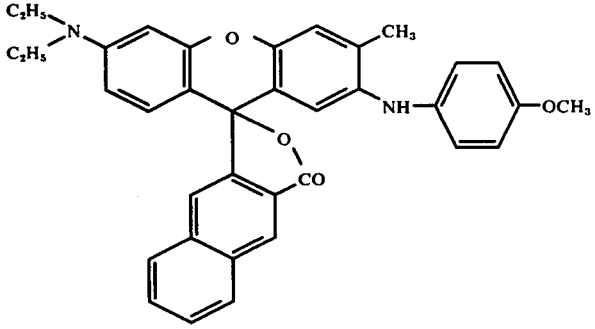 | Reddish black |
| 16 | 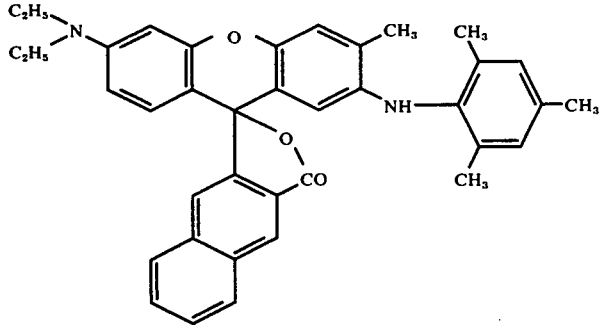 | Reddish black |
| 17 | 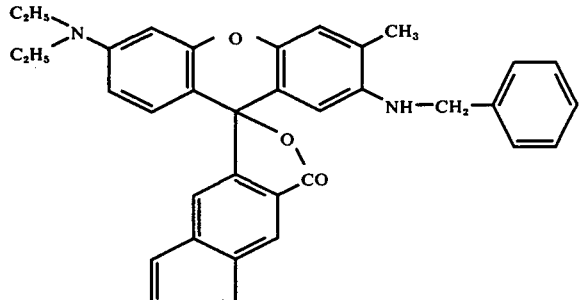 | Reddish black |
| 18 | 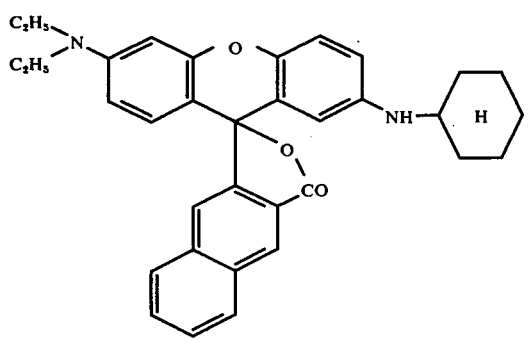 | Greenish black |

-continued

| Compound No. | Chemical formula | Shade on silica gel |
|---|---|---|
| 19 | | Greenish black |
| 20 | | Violet black |
| 21 | | Greenish black |
| 22 | | Greenish black |

-continued

| Compound No. | Chemical formula | Shade on silica gel |
|---|---|---|
| 23 | | Dark greenish black |
| 24 | | Greenish black |
| 25 | | Green |
| 26 | | Green |

-continued

| Compound No. | Chemical formula | Shade on silica gel |
|---|---|---|
| 27 | 3-diethylamino-7-(N,N-diallylamino) spiro-naphthalide structure with $(C_2H_5)_2N$— and —$N(CH_2$—$CH$=$CH_2)_2$ groups | Green |
| 28 | analogous structure with —$N(CH_2$—$C$≡$CH)_2$ group | Green |
| 29 | analogous structure with —$NH_2$ group on naphthalene | Dark red |
| 30 | analogous structure with —NH-(2,4,6-trimethylphenyl) group | Green |

-continued

| Compound No. | Chemical formula | Shade on silica gel |
|---|---|---|
| 31 | | |
| 32 | | Green |
| 33 | | Green |
| 34 | | Dark red |

-continued

| Compound No. | Chemical formula | Shade on silica gel |
|---|---|---|
| 35 | | Green |
| 36 | | Green |
| 37 | | Green |
| 38 | | Dark green |

-continued
| Compound No. | Chemical formula | Shade on silica gel |
|---|---|---|
| 39 | 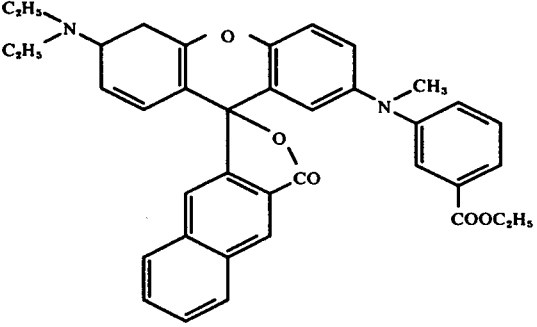 | Greenish brown |
| 40 | 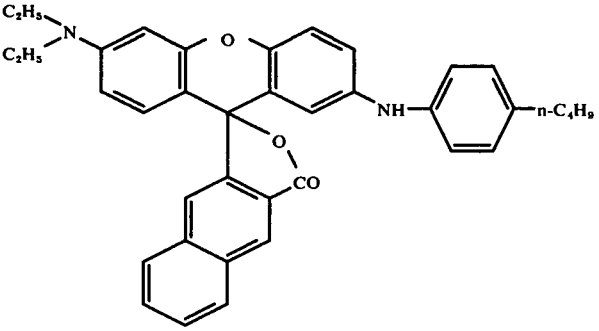 | Greenish black |
| 41 | 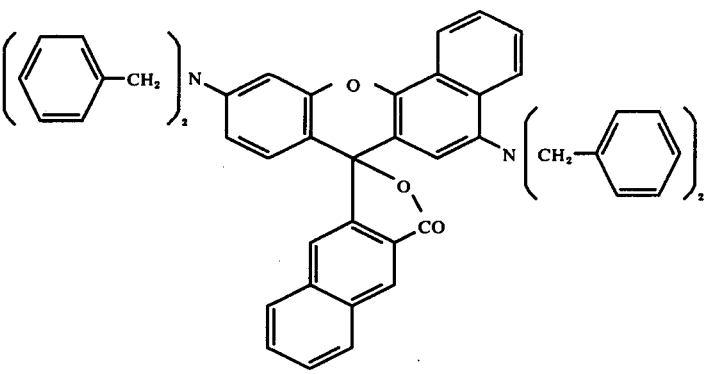 | Dark red |
| 42 | 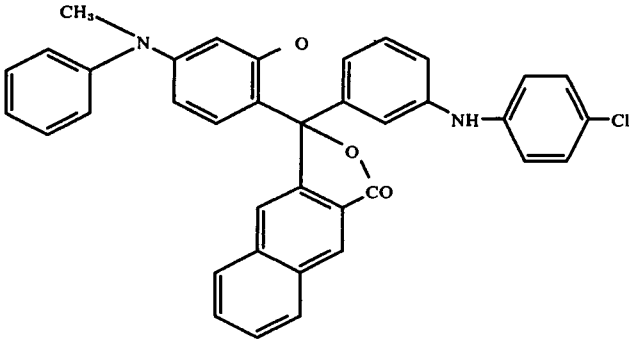 | Dark green |

-continued

| Compound No. | Chemical formula | Shade on silica gel |
|---|---|---|
| 43 | | Dark green |
| 44 | | Dark greenish black |
| 45 | | Greenish black |
| 46 | | Black brown |

-continued

| Compound No. | Chemical formula | Shade on silica gel |
|---|---|---|
| 47 | | Black brown |
| 48 | | Black brown |
| 49 | | Black green |
| 50 | | Greenish black |

-continued

| Compound No. | Chemical formula | Shade on silica gel |
|---|---|---|
| 51 | | Greenish black |
| 52 | | Reddish black |
| 53 | | Green |
| 54 | | Green |

-continued

| Compound No. | Chemical formula | Shade on silica gel |
|---|---|---|
| 55 | | Green |
| 56 | | Black violet |
| 57 | | Greenish black |
| 58 | | Greenish black |

-continued

| Compound No. | Chemical formula | Shade on silica gel |
|---|---|---|
| 59 | | Greenish black |
| 60 | | Bluish black |
| 61 | | Dark green |
| 62 | | Dark green |

-continued

| Compound No. | Chemical formula | Shade on silica gel |
|---|---|---|
| 63 | | Reddish black |
| 64 | | Green |
| 65 | | Green |
| 66 | | Reddish black |

-continued

| Compound No. | Chemical formula | Shade on silica gel |
|---|---|---|
| 67 | | Black green |
| 68 | | Greenish black |
| 69 | | Reddish brown |
| 70 | | Dark green |

| Compound No. | Chemical formula | Shade on silica gel |
|---|---|---|
| 71 | | Dark green |
| 72 | | Black green |

Among the compounds in the Table having good properties as a coloring matter for pressure-sensitive or heat-sensitive copying paper, the compounds which are more favorable in the properties are those represented by the following formula,

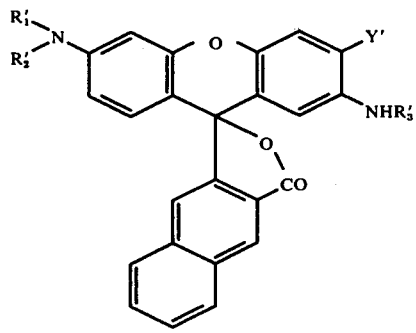

wherein $R_1'$ and $R_2'$ are each methyl, ethyl or cyclohexyl, $R_3'$ is cyclohexyl or

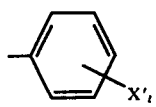

in which X' is lower alkyl and $l$ is as defined above, and Y' is hydrogen or lower alkyl.

More prticularly, the compounds among them which are particularly superior in light fastness are those represented by the following formula,

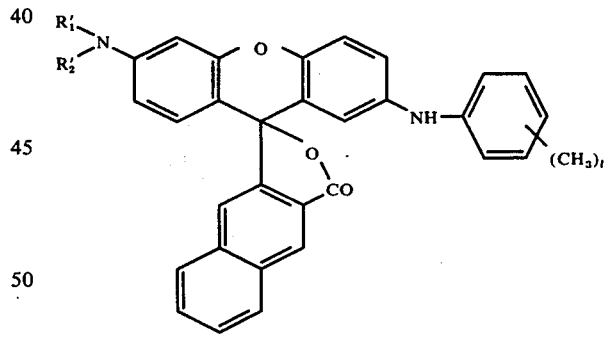

wherein $R_1'$ and $R_2'$ are as defined above and $l$ is as defined above and preferably is 2 to 3.

In order to clarify the said superiority, the results concerning the light fastness test made on the following eight compounds (the present compounds and references) according to the method as mentioned below are given as follows:

No. 3
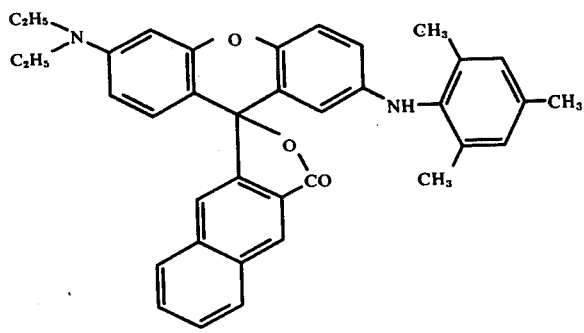
No. 4
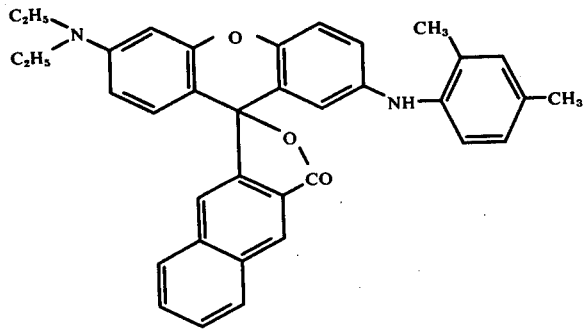
No. 50
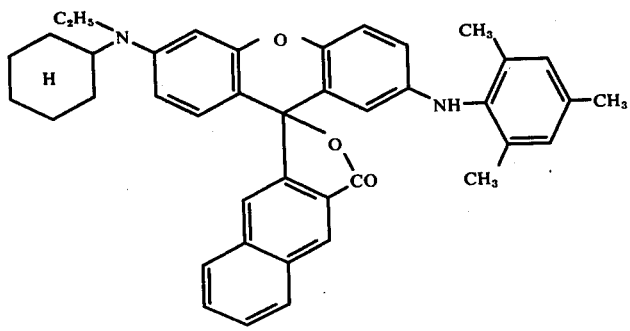
No. 51
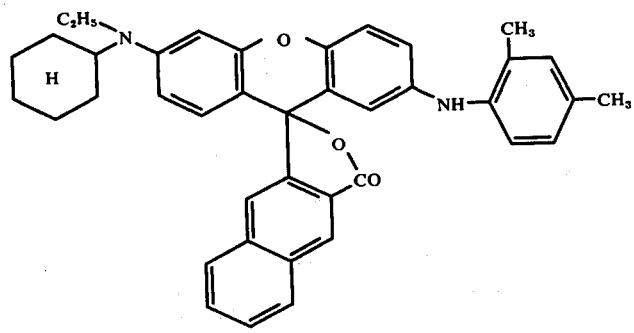
No. 5
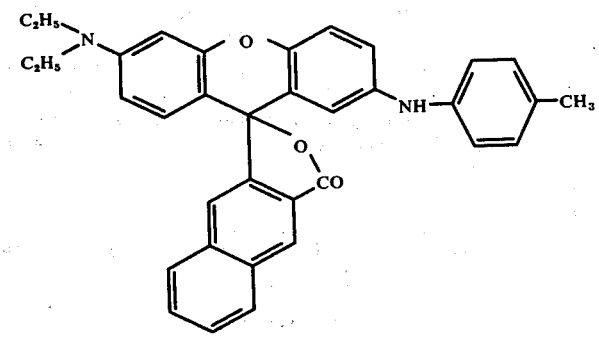

-continued

No. 8

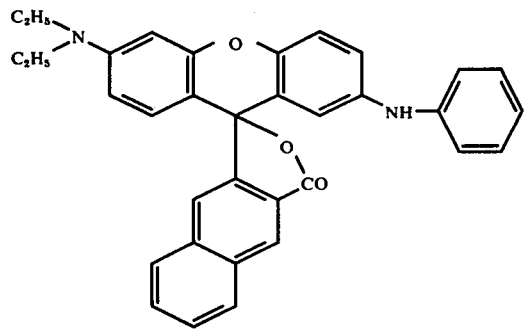

Reference 1

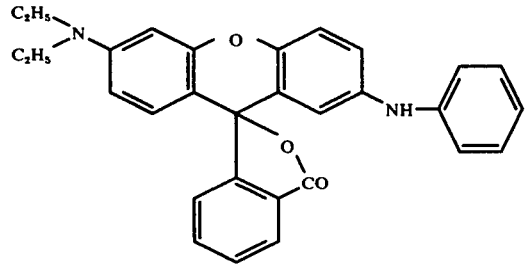

Reference 2

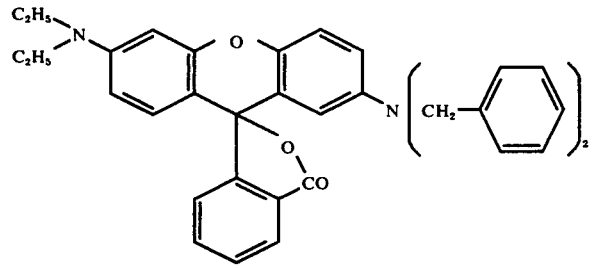

Light-fastness test:
1. Acidic substance-coated front paper is first prepared. 0.1 Gram of each fluoran compound is weighed accurately and dissolved completely in 10.0 ml of toluene accurately weighed. One ml of the toluene solution is taken on the coated surface of the front paper by means of a whole pipette, and coated on the paper by means of a bar coater No. 5 whereby a color is developed on the paper by the reaction between the acidic substance and the fluoran compound.

2. The initial color depth ($C_o$) is determined on a Mac Beth Densitometer (manufactured by Mac Beth Co.), and then the paper is exposed to a xenon lamp. Changes in color depth are determined on the Densitometer at 2, 4, 7, 10, 15, 20 and 30 minutes after the beginning of exposure. The values are expressed by C(t), a function of exposure time.

3. A value, f(t), calculated from the following equation means a percentage of depth-retention after $t$ minutes of exposure time.

$$f(t) = \frac{C(t)}{C_o} \times 100$$

Larger values of f(t) mean a higher light-fastness. The test results are as shown in the accompanying drawing.

Furthermore, among the fluoran compounds which develop a black color in the form of a single compound, the so-called "homogeneous black," the compounds which are particularly superior in a black tone and its depth are those represented by the following formula,

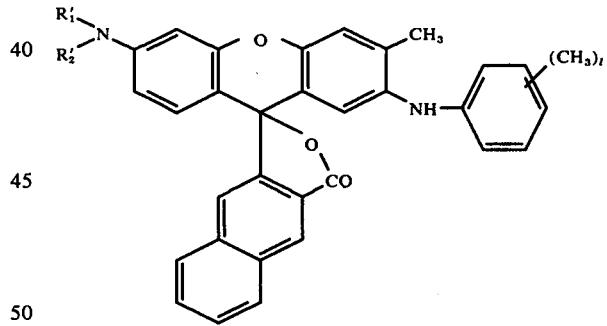

wherein $R_1'$ and $R_2'$ are as defined above, and $l$ is as defined above, and preferably 1 or 2.

In order to clarify the said superiority, the following test results are given.

The compounds Nos. 12, 14 and 52, the abovementioned compounds Nos. 3, 4, 5, 8, 50, 51, references 1 and 2, are each coated, in the form of a 1% toluene solution, on front paper coated with acid clay, and the developed color obtained and its initial depth on a Mac Beth Densitometer are summarized in the following Table.

| Compound No. | Initial color depth on Mac Beth Densitometer | Color developed on acid Clay |
|---|---|---|
| 12 | 0.85 | Black |
| 14 | 0.80 | Reddish black |

-continued

| Compound No. | Initial color depth on Mac Beth Densitometer | Color developed on acid Clay |
| --- | --- | --- |
| 52 | 0.82 | Black |
| 3 | 0.78 | Greenish black |
| 4 | 0.78 | Greenish black |
| 50 | 0.76 | Greenish black |
| 51 | 0.77 | Greenish black |
| 5 | 0.74 | Greenish black |
| 8 | 0.75 | Greenish black |
| Reference 1 | 0.74 | Green |
| Reference 2 | 0.76 | Black green |

As used in mark-forming systems, marking in desired areas on support webs or sheets may be accomplished by effecting localized reactive contact between the chromogenic material and the acidic material on or in such web or sheet, such chromogenic material being brought thereto by transfer, or already present therein, the reactive contact forming a clear coloration in the intended image-marking areas.

There have already been known several types of recording system utilizing an electron donor-acceptor color-forming reaction between a chromogenic material and an acidic material.

The pressure-sensitive recording systems generally comprise color-forming components on and/or within one or more sheet supports, the color-forming components being isolated fron one another by a pressure-rupturable barrier. Where the color-forming components are disposed on separate sheets as disclosed in U.s. Pat. No. 2,712,507, the record material is referred to as a "transfer" or "couplet" system. In such system, a solution of a chromogenic material is held in rupturable microscopic capsules coated onto one surface of a transfer sheet, while an adjacent receiving sheet is sensitized with an acidic material, i.e. an electron acceptor. Most common acidic materials are activated acid clay and acid clays, such as attapulgite, zeolite, bentonite, kaolin and silica. Recently, monomeric phenols or acid reactant polymeric materials, such as phenolic polymers, phenol acetylene polymers, maleic acid-rosin resins have been suggested either alone or in combination with acid clays.

In the manufacturing method of such a record material, for instance, a non-volatile oil containing a chromogenic material dissolved therein is protected by encapsulation with coacervate film of a water-soluble polymer. The resulting coating composition containing dispersed capsules are coated on one side of a sheet, and coating composition of said electron-acceptors is coated on the other side of the sheet. When several sheets are laid on over another and impressed with a pencil or the like, capsules are collapsed to release the oil containing the chromogenic material which produces a duplicated image on contact with the electronacceptor. In another system as disclosed in U.S. Pat. No. 2,730,457, a coating liquid containing both of the capsules chromogenic material and acidic material is applied on one side of a sheet or alternatively, a coating containing capsules is first applied on one side of a sheet and the second coating containing the electronacceptor is applied thereon. Thus, all the components are disposed on a single sheet, the record material is referred to as "self-contained" system and deveops image color when the pressure is applied.

As a modification of pressure-sensitive marking system, Japanese Pat. No. 511,757 (corresponds to U.S. Pat. Application Ser. No. 392,404, filed on Aug. 27, 1964) discloses a recording sheet, in which minute capsules containing a liquid solvent are coated on one surface of a sheet support and both of the chromogenic material and the acidic polymer are coated on or impregnated in the same sheet or other sheet in solid condition.

There is thermo-responsive record sheet as a mark-forming system utilizing an electron donor-acceptor color-forming reaction. For example, Japanese Pat. Publication No. 45-14039 (corresponds to U.S. Pat. Application Ser. No. 554,565 filed on June 1, 1966) discloses a temperature-responsive record material comprising a supporting sheet material having crystal violet lactone and a phenolic material solid at room temperature but capable of liquefying and/or vaporizing at normal thermographic temperatures, said lactone and phenolic material being further capable of effecting a mark-forming reaction upon reactive contact.

The novel compounds of the present invention are widely used for the above-mentioned mark-forming systems as a colorless chromogenic compound, i.e., an electron donor and gives many excellent advantages.

According to the present invention, the above-mentioned known techniques for the production of the recording sheet are utilized using the abovementioned fluoran compounds as a coloring material alone or in admixture with various known coloring materials to obtain the recording sheet which can form red, green or black color.

Also, it is effective for improving the color forming property and fastnesses to light and moisture of developed images to use a metal or metallic compound together with the electron acceptor.

Thus, metals or metallic compounds such as manganese, nickel, cobalt, iron, zinc, copper, cadmium, mercury, silver, platinum, etc. are effective. Specific examples of the metallic compounds include salts and acid salts such as copper sulfate, ferrous sulfate, manganese sulfate, cobalt sulfate, zinc sulfate, nickel acetate, etc.; basic salts such as cadmium hydroxide; and oxides such as zinc oxide. They show particularly good results.

The present invention will be illustrated with reference to the following examples, which are only given for the purpose of illustration and not to be interpreted as limiting thereto. All parts and % in the examples are by weight unless otherwise stated.

EXAMPLE 1

In 200 parts of a 90% sulfuric acid were dissolved 10.9 parts of 4-aminophenol and 36.3 parts of 2-(4'-diethylamino-2'-hydroxy)benzoylnaphthalene-3carboxylic acid at a temperature below 20° C. The solution was kept while stirring at 20° to 30° C for about 10 hours to complete the reaction, and then the solution was poured, or hydroylsis, into 2 liters of ice water. The separated black precipitate was filtered, thoroughly washed with water, neutralized with 1.5 liters of a 5% aqueous casutic soda while stirring and then filtered again.

The precipitate thus obtained was dissolved in 750 parts of toluene and the solution was decolorized with 5 parts of active carbon, dried and concentrated until crystals separated out.

Thus, a coloring matter of good lightfastness represented by the formula

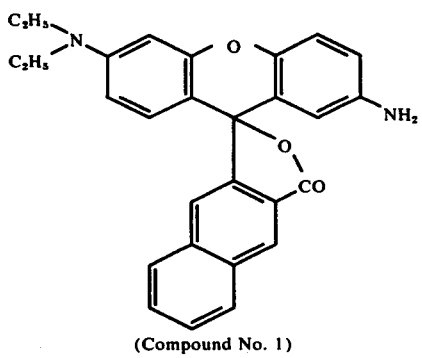

(Compound No. 1)

was obtained as pale red crystals in a yield of 41% (m.p. 111°–113° C). The matter developed a black brown color on contacting with silica gel. Elementary analysis of the compound No. 1 agreed very closely with the calculated values.

|  | C | H | N |
|---|---|---|---|
| Calculated (%) | 77.1 | 5.5 | 6.4 |
| Found (%) | 77.0 | 5.9 | 6.5 |

EXAMPLE 2

In a four-necked flask equipped with a stirrer, a thermometer and a condenser were placed 140 parts of a 95% sulfuric acid, and then 12.5 parts of 4-mesidinophenol were dissolved at a temperature below 20° C while ice-cooling. Next, 20 parts of 2-(2'-hydroxy-4'-diethylamino)benzoylnaphthalene-3-carboxylic acid were dissolved in the same manner as described above, and then the solution was kept at 70° to 80° C for about 5 hours while stirring. After completion of the reaction, the reaction solution was cooled and then poured, for hydrolysis, into 2 liters of ice water. The separated black precipitate was filtered, thoroughly washed with water, neutalized with 1.5 liters of 5% aqueous caustic soda while stirring and then filtered again. The precipitate thus obtained was dissolved in 750 parts of toluene, and the solution was clarified with 5 parts of active carbon, dried and concentrated until crystals separated out.

After recrystallization from iso-propylalcohol, a coloring matter of good light fastness represented by the formula,

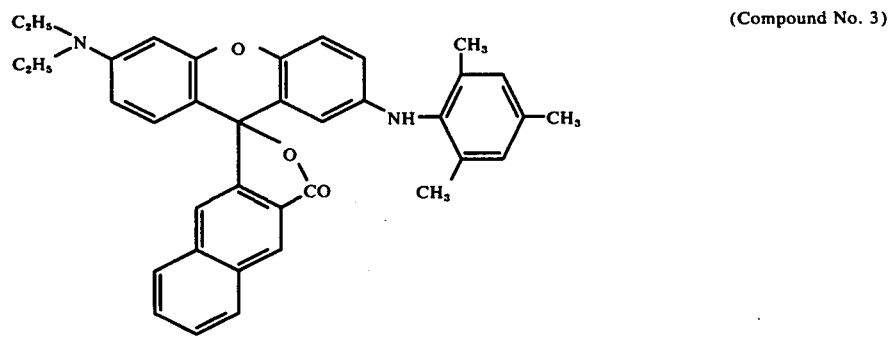

(Compound No. 3)

was obtained as pale pink crystals in a yield of 49% (m.p. 152.2°–154° C). The matter developed a greenish black color on contacting with silica gel.

The following compounds were obtained in the same manner as described in Example 1 or 2.

| Compound No. | Chemical formula | Yield (%) | Melting point (° C) | Shade on silica gel |
|---|---|---|---|---|
| 4 | ![structure] | 43.6 | 176–179 | Greenish black |

-continued

| Compound No. | Chemical formula | Yield (%) | Melting point (°C) | Shade on silica gel |
|---|---|---|---|---|
| 5 | [structure: xanthene with C₂H₅₂N-, NH-C₆H₄-CH₃ (para), naphthalene-CO-O lactone] | 47.5 | 175–176 | Greenish black |
| 6 | [structure: xanthene with C₂H₅₂N-, NH-C₆H₄-CH₃ (ortho), naphthalene-CO-O lactone] | 23.5 | 203.5–205 | Black brown |
| 8 | [structure: xanthene with C₂H₅₂N-, NH-C₆H₅, naphthalene-CO-O lactone] | 45 | 183–185 | Black |

Elementary analysis of the compounds agreed very closely with the calculated values.

| Compound No. | | C | H | N |
|---|---|---|---|---|
| 3 | Calculated (%) | 80.1 | 6.1 | 5.1 |
| | Found (%) | 80.2 | 6.5 | 5.1 |
| 4 | Calculated (%) | 80.0 | 5.9 | 5.2 |
| | Found (%) | 79.3 | 6.0 | 5.3 |
| 5 | calculated (%) | 79.8 | 5.7 | 5.3 |
| | Found (%) | 80.2 | 5.8 | 5.6 |
| 6 | Calculated (%) | 79.8 | 5.7 | 5.3 |
| | Found (%) | 80.1 | 5.6 | 5.5 |
| 8 | Calculated (%) | 79.7 | 5.5 | 5.5 |
| | Found (%) | 79.6 | 5.8 | 5.4 |

EXAMPLE 3

To 100 parts of 98% sulfuric acid were added 36.3 parts of 2-(2'-hydroxy-4'-diethylamino)benzoylnaphthalene-3-carboxylic acid and 19.9 parts of 4-p-toluidino-m-cresol at a temperature below 20° C and the solution was kept at 25° to 30° C for 6 hours. After completion of the reaction, separation and purification were carried out in the same manner as described in Example 1. Thus, a coloring matter of good light fastness represented by the formula,

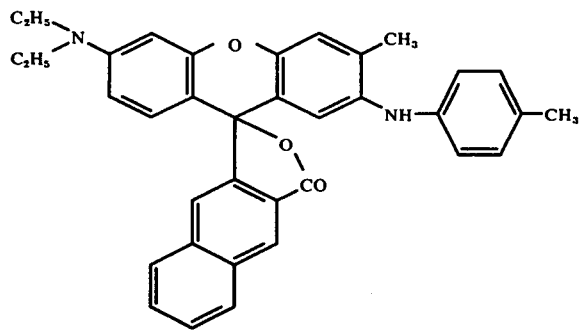

was obtained as pale orange crystals in a yield of 67% (m.p. 131°–132° C). The matter developed reddish black color of high depth on silica gel. Elementary analysis of the compound No. 12 agreed very closely with the calculated values.

|  | C | H | N |
|---|---|---|---|
| Calculated (%) | 80.0 | 6.0 | 5.2 |
| Found (%) | 79.8 | 5.9 | 5.3 |

The compounds No. 13 to No. 16 were obtained in completely the same manner as described in Example 3. All the compounds were pale crystals which developed a reddish black color on contacting with silica gel. Melting points were as follows:

| Compound No. | Melting point (° C) | Shade on silica gel |
|---|---|---|
| 13 | 140–141 | Reddish black |
| 14 | 133–134 | Reddish black |
| 15 | 128–129 | Reddish black |
| 16 | 130–132 | Reddish black |

EXAMPLE 4

In the similar manner to that described in Example 2, 27.5 parts of 4-(N-benzyl-N-phenyl)aminophenol and 36.3 parts of 2-(4'-diethylamino-2'-hydroxy)benzoyl-naphthalene-3-carboxylic acid were dissolved in 220 parts of 95% sulfuric acid and condensed with each other. The resulting product was purified from toluene to obtain a compound represented by the formula,

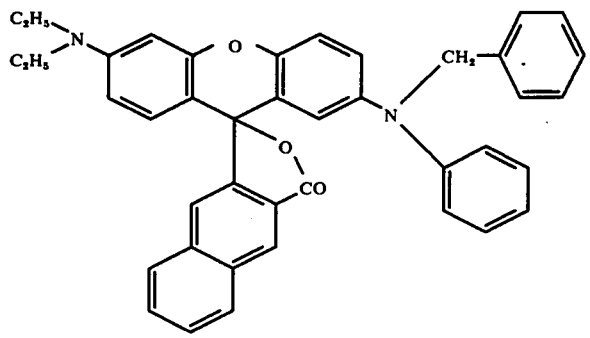

(Compound No. 10)

as pale pink crystals in a yield of 40% (m.p. 186°–190° C). The compound developed a dark greenish black color on silica gel. Elementary analysis of the compound No. 10 agreed very closely with the calculated values.

|  | C | H | N |
|---|---|---|---|
| Calculated (%) | 81.7 | 5.6 | 4.7 |
| Found (%) | 81.5 | 5.9 | 4.6 |

EXAMPLE 5

Ten parts of the compound No. 45 was dissolved in 100 parts of dimethylformamide, and then 1.1 parts of soda ash was added thereto. The solution was heated to 45° to 50° C at which 7.7 parts of diethyl sulfate were added dropwise, and then the solution was kept at 45° to 50° C for 3 hours. After the reaction was completed, the reaction solution was discharged in aqueous dilute caustic soda, and the separated precipitate was filtered. The precipitate thus obtained was dissolved in toluene, and the toluene solution was clarified with active carbon and concentrated and n-hexane was added to the residue to obtain crystals.

Thus, a compound represented by the formula,

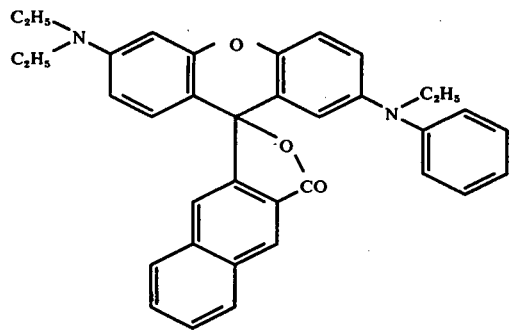

(Compound No. 11)

was obtained as pale pink crystals in a yield of 43% (m.p. 189°–191° C). The compound developed a black brown color on contacting with silica gel.

EXAMPLE 6

A compound represented by the formula,

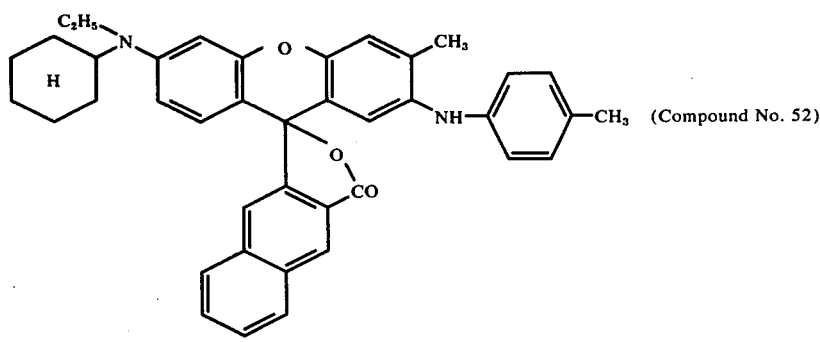
(Compound No. 52)

In the same manner as described in Example 5, a compound represented by the formula,

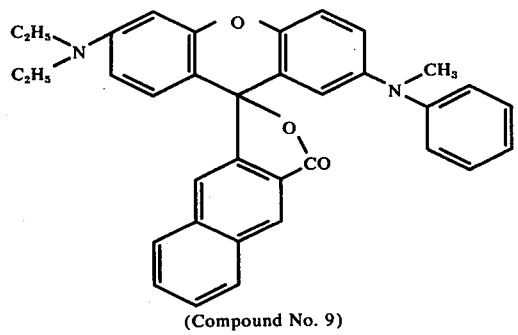
(Compound No. 9)

was obtained as pale pink crystals in a yield of 38% (m.p. 194°–195° C). The compound developed a black brown color on silica gel. Elementary analysis of the compounds Nos. 11 and 9 agreed very closely with the calculated values as follows:

| No. 11 | | | |
|---|---|---|---|
| | C | H | N |
| Calculated (%) | 80.0 | 5.9 | 5.2 |
| Found (%) | 79.8 | 6.0 | 5.3 |

| No. 9 | | | |
|---|---|---|---|
| | C | H | N |
| Calculated (%) | 79.9 | 5.7 | 5.3 |
| Found (%) | 79.2 | 5.7 | 5.6 | was obtained as pale yellow crystals (m.p. 179°–181° C) in a yield of 23% from 21.3 parts of 4-(p-toluidino)3-methylphenol and 41.8 parts of 2-[4′-(N-cyclohexylN-ethyl)amino-2′-hydroxy]benzoylnaphthalene-3-carboxylic acid in the same manner as described in Example 1, except that 100% polyphosphoric acid was used in place of 90% sulfuric acid. The compound thus obtained developed a dull greenish black color on contacting with silica gel. Elementary analysis of the compound No. 52 agreed very closely with the calculated values.

| | C | H | N |
|---|---|---|---|
| Calculated (%) | 80.8 | 6.4 | 4.7 |
| Found (%) | 80.2 | 6.6 | 4.7 |

EXAMPLE 7

In 200 parts of 90% sulfuric acid were dissolved 32.5 parts of 4-(2′-o-methylphenoxy)anilinonaphthol and 36.3 parts of 2-(4′-diethylamino-2′-hydroxy)benzoylnaphthalene-3-carboxylic acid at a temperature below 20° C. The solution was kept while stirring at 20 to 30° C for about 10 hours to complete the reaction, and then the solution was poured, for hydrolysis, into 2 liters of ice water. The separated black precipitate was filtered, thoroughly washed with water, neutralized with 1.5 liters of 5% aqueous caustic soda while stirring and then filtered again. The precipitate thus obtained was dissolved in 750 parts of toluene, the solution was clarified with 5 parts of active carbon, dried and concentrated until crystals separated out.

Thus, a compound represented by the formula,

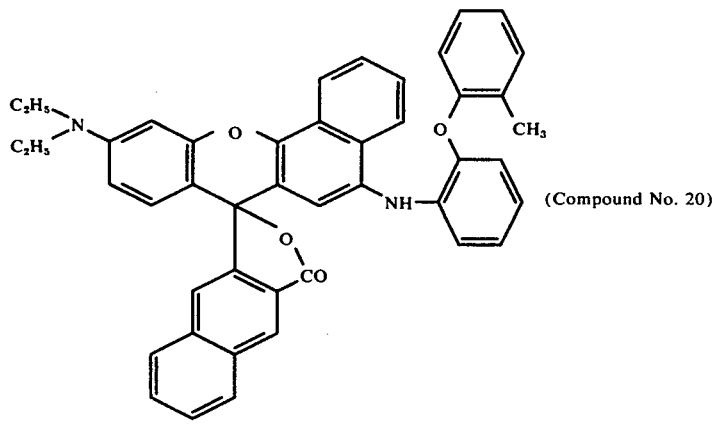

(Compound No. 20)

was obtained as pale green crystals in a yield of 52% (m.p. 198°–200° C). The compound developed a violet black color on silica gel. Elementary analysis of the compound No. 20 agreed very closely with the calculated values.

|  | C | H | N |
|---|---|---|---|
| Calculated (%) | 80.8 | 5.4 | 4.2 |
| Found (%) | 80.5 | 5.4 | 4.3 |

EXAMPLE 8

In 100 ml of dimethylformamide was dissolved 8.7 parts of the fluoran compound obtained in Example 1, and 1.1 parts of soda ash was added thereto. The solution was heated to 50° to 55° C at which 8.2 parts of benzyl bromide was added dropwise, and then the solution was kept at 50° to 55° C for 5 hours. After the reaction was completed, the solution was discharged in aqueous dilute caustic soda and the separated precipitate was filtered and washed with water. The precipitate thus obtained was dissolved in toluene and the toluene solution was clarified with active carbon and concentrated, and n-hexane was added to the residue to obtain crystals.

Thus, a compound represented by the formula, was obtained as pale green crystals in a yield of 65.5% (m.p. 86°–88° C). The compound developed a green color on contacting with silica gel.

Elementary analysis of the compound No. 36 agreed very closely with the calculated values.

|  | C | H | N |
|---|---|---|---|
| Calculated (%) | 81.8 | 5.8 | 4.5 |
| Found (%) | 82.3 | 6.0 | 4.3 |

EXAMPLE 9

In 200 parts of 105% phosphoric acid were dissolved 22.0 parts of 4-(p-chlorophenyl)aminophenol and 43.1 parts of 2-[4'-(N-methyl-N-phenyl)amino-2'hydroxy]-benzoylnaphthalene-3-carboxylic acid at a temperature below 20° C. The solution was kept while stirring at 70° to 80° C for about 10 hours to complete the reaction, and then the solution was poured, for hydrolysis, into 2 liters of ice water. The separated black precipitate was filtered, thoroughly washed with water, neutralized with 1.5 liters of 5% aqueous caustic soda while stirring and then filtered again. The precipitate thus obtained was dissolved in 750 parts of toluene, and the solution was clarified with 5 parts of active carbon, dried and concentrated until crystals separated out.

Thus, a compound represented by the formula,

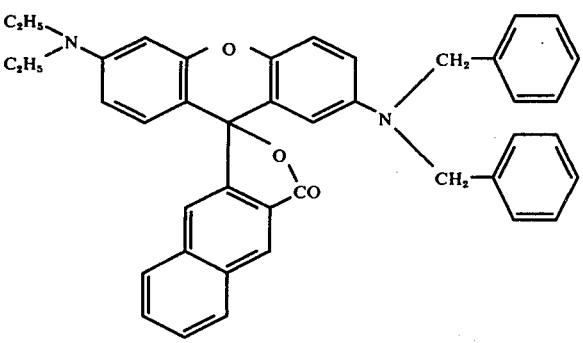

(Compound No. 36)

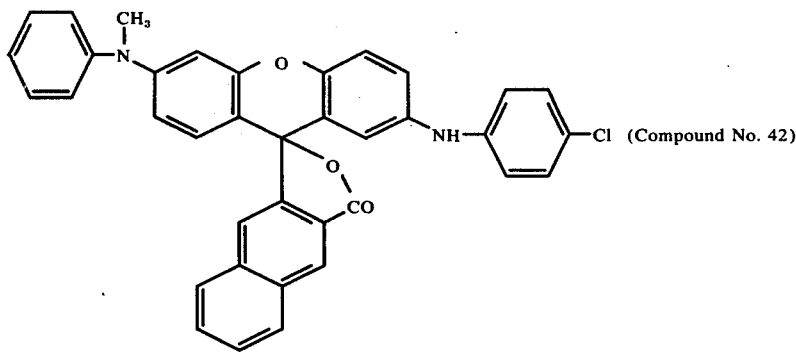
(Compound No. 42)

was obtained as pale green crystals in a yield of 23.8% (m.p. 205°–207° C). The compound developed a dark green color on silica gel. Elementary analysis of the compound No. 42 agreed closely with the calculated values.

|  | C | H | N | Cl |
|---|---|---|---|---|
| Calculated (%) | 76.5 | 4.5 | 4.8 | 6.1 |
| Found (%) | 76.2 | 4.3 | 4.7 | 6.0 |

EXAMPLE 10

In the same manner as described in Example 7, 27.3 parts of 4-(2'-o-methylphenoxy)anilinophenol and 38.0 parts of 2-(4'-pyrrolyl-2'-hydroxy)benzolnaphthalene3-carboxylic acid were condensed together and purified.

Thus, a compound represented by the formula,

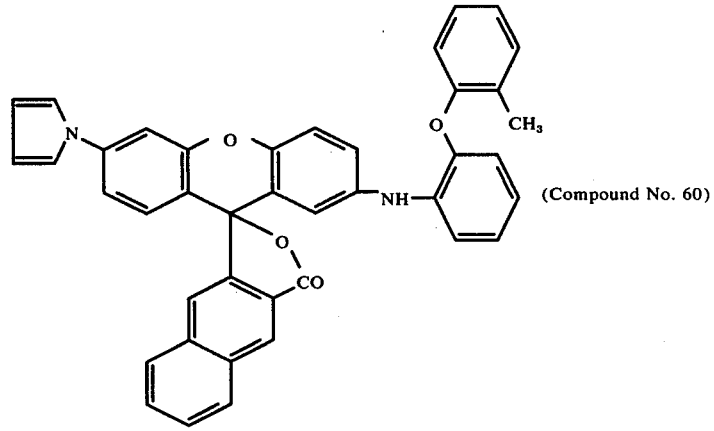
(Compound No. 60)

was obtained as pale blue crystals in a yield of 38.4% (m.p. 207.5°–210° C).

The compound developed a bluish black color on silica gel. Elementary analysis of the compound No. 60 agreed very closely with the calculated values as follows:

|  | C | H | N |
|---|---|---|---|
| Calculated (%) | 80.4 | 4.6 | 4.6 |
| Found (%) | 80.1 | 4.8 | 4.5 |

EXAMPLE 11

In the similar manner to that described in Examples 1 and 2, 36.3 parts of 2-(4'-diethylamino-2'hydroxy)benzoylnaphthalene-3-carboxylic acid and 17.7 parts of p-cyclohexylaminophenol were dissolved in 200 parts of 98.0% sulfuric acid and condensed together followed by purification from toluene.

Thus, a compound represented by the formula,

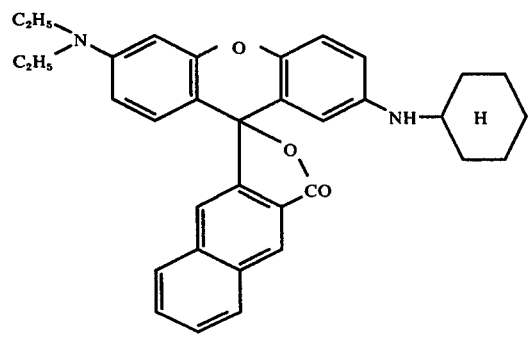

(Compound No. 18)

was obtained as pale pink crystals in a yield of 48% (m.p. 126°–128° C). The compound developed a greenish black color on contacting with silica gel. Elementary analysis of the compound No. 18 agreed very closely with the calculated values as follows:

| | C | H | N |
|---|---|---|---|
| Calculated (%) | 78.7 | 6.6 | 5.4 |
| Found (%) | 78.6 | 6.7 | 5.5 |

In the same manner as in Example 11, compound No. 19 represented by the formula,

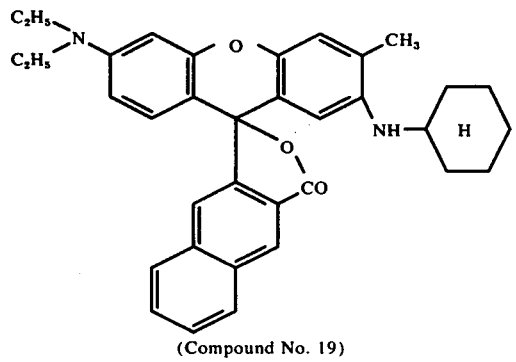

(Compound No. 19)

was obtained in a yield of 42% (m.p. 110°–112° C).

| | C | H | N |
|---|---|---|---|
| Elementary analysis: Calculated (%) | 78.9 | 6.8 | 5.3 |
| Found (%) | 78.7 | 6.9 | 5.2 |

EXAMPLE 12

In the same manner as described in Examples 1 and 2, a coloring matter of good light fastness represented by the formula,

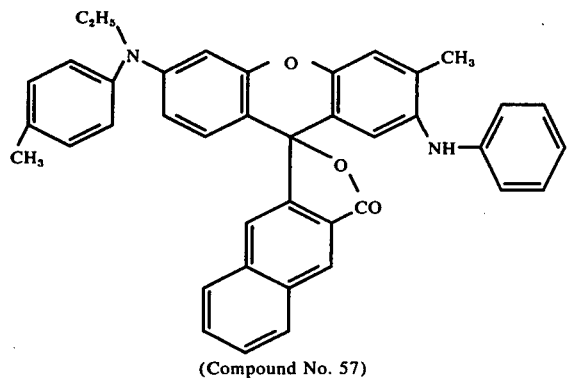

(Compound No. 57)

was obtained as pale orange crystals in a yield of 28.0% (m.p. 196°–198° C) from 19.9 parts of 4-phenylamino-m-cresol and 42.1 parts of 2-(4'-N-ethyl-N-p-tolyl-2'-hydroxy)benzoylnaphthalene-3-carboxylic acid.

The compound developed a greenish black color on silica gel. Elementary analysis of the compound No. 57 agreed very closely with the calculated values as follows:

| | C | H | N |
|---|---|---|---|
| Calculated (%) | 81.6 | 5.5 | 4.7 |
| Found (%) | 81.3 | 5.6 | 4.5 |

EXAMPLE 13

In the similar way to that described in Examples 1 and 2, 18.5 parts of p-phenylaminophenol and 41.7 parts of 2-[4'-(N-cyclohexyl-N-ethyl)amino-2'-hydroxy]benzoylnaphthalene-3-carboxylic acid were dissolved in 200 parts of 98% sulfuric acid and condensed together followed by purification from toluene.

Thus, a compound represented by the formula,

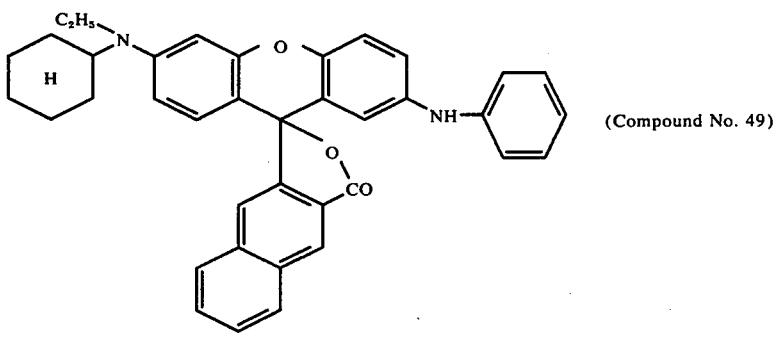

(Compound No. 49)

was obtained as pale pink crystals in a yield of 38% (m.p. 196°–198° C). The compound developed a black green color on silica gel. Elementary analysis of the compound No. 49 agreed very closely with the calculated values.

| | C | H | N |
|---|---|---|---|
| Calculated (%) | 80.5 | 6.1 | 4.9 |
| Found (%) | 80.2 | 6.3 | 4.8 |

In the same manner as in Example 13, compounds Nos. 50, 51 and 53 represented by the formulas,

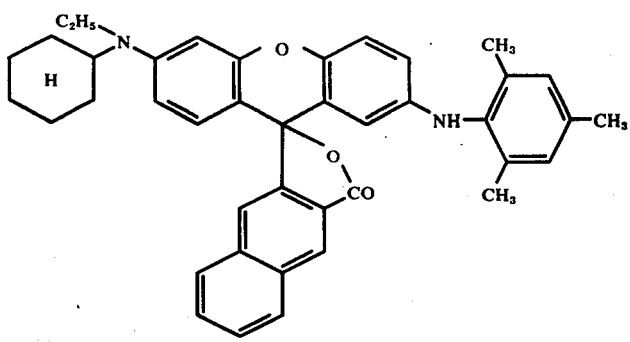

(Compound No. 50)

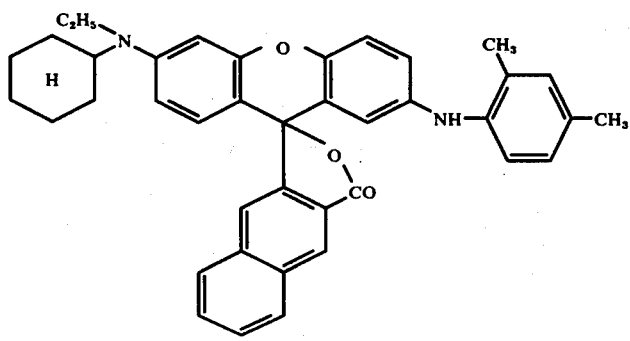

(Compound No. 51)

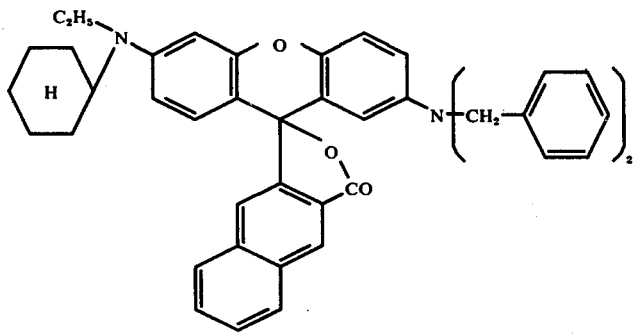

(Compound No. 53)

were obtained.

Melting point:

| Compound No. | Melting point (° C) |
|---|---|
| 50 | 130 – 132 |
| 51 | 187 – 189 |
| 53 | 91 – 93 |

Elementary analysis:

| Compound No. | | C | H | N |
|---|---|---|---|---|
| 50 | Calculated (%) | 80.9 | 6.6 | 4.6 |
| | Found (%) | 80.7 | 6.7 | 4.5 |
| 51 | Calculated (%) | 80.8 | 6.4 | 4.7 |
| | Found (%) | 80.7 | 6.4 | 4.6 |
| 53 | Calculated (%) | 82.4 | 6.3 | 4.2 |
| | Found (%) | 82.2 | 6.4 | 4.2 |

EXAMPLE 14

In the similar manner to that described in Examples 1 and 2, 19.9 parts of p-toluidinophenol and 37.7 parts of 2-(4'-morpholino-2'-hydroxy)benzoylnaphthalene-3-carboxylic acid were dissolved in 200 parts of 96% sulfuric acid and condensed together followed by purification from toluene.

Thus, a compound represented by the formula,

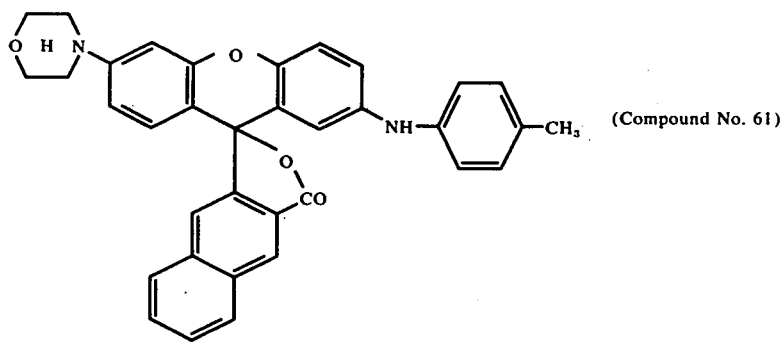

(Compound No. 61)

was obtained as pale yellow crystals in a yield of 48% (m.p. 205°–207° C). The compound developed a dark green color on contacting with silica gel. Elementary analysis of the compound No. 61 agreed very closely with the calculated values.

|  | C | H | N |
|---|---|---|---|
| Calculated (%) | 77.8 | 5.2 | 5.2 |
| Found (%) | 78.0 | 5.1 | 5.2 |

In the same manner as in Example 14, compounds a Nos. 62, 63 and 64 represented by the formulas,

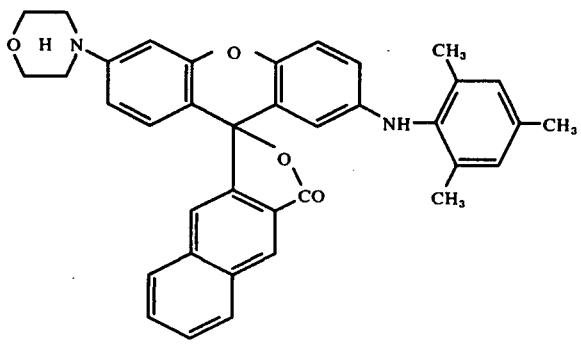

(Compound No. 62)

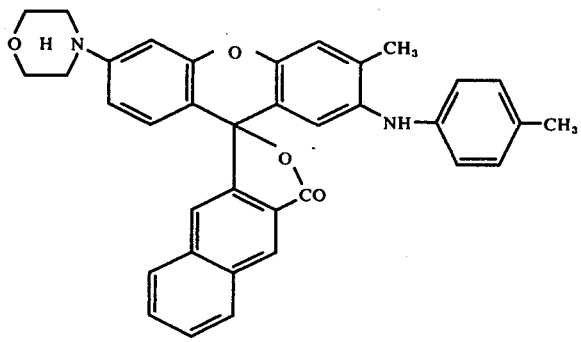

(Compound No. 63)

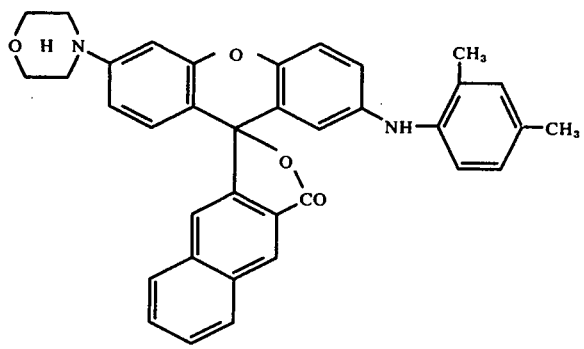

(Compound No. 64)

were obtained. The following tables show melting points, colors developed on silica gel and results of elementary analysis.

| Compound No. | Melting point (° C) | Shade on Silica gel |
|---|---|---|
| 62 | 215 – 217 | Dark green |
| 63 | 202 – 204 | Reddish black |
| 64 | 210 – 212 | Green |

| Compound No. | | C | H | N |
|---|---|---|---|---|
| 62 | Calculated (%) | 78.1 | 5.7 | 4.9 |
|  | Found (%) | 78.0 | 5.8 | 4.8 |
| 63 | Calculated (%) | 78.0 | 5.4 | 5.0 |
|  | Found (%) | 77.8 | 5.3 | 5.1 |
| 64 | Calculated (%) | 79.5 | 5.3 | 4.6 |
|  | Found (%) | 79.3 | 5.3 | 4.5 |

EXAMPLE 15

In the similar way to that described in Examples 1 and 2, 18.5 parts of p-phenylaminophenol and 52.1 parts of 2-(4'-diethylamino-2'-hydroxy)benzoyl-5,8-dibromonaphthalene-3-carboxylic acid were dissolved in 250 parts of 98% sulfuric acid and condensed together followed by purification from toluene.

Thus, a compound represented by the formula,

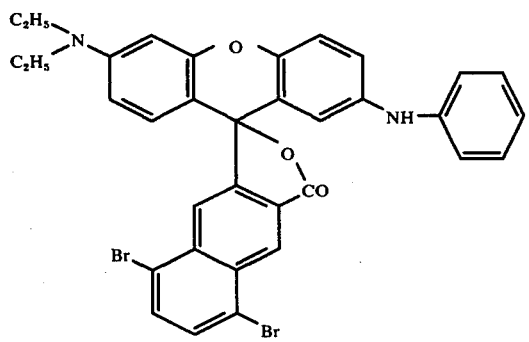

(Compound No. 68 was obtained as pale green crystals in a yield of 37% (m.p. 236°–238° C). The compound developed a dark green color on silica gel. Elementary analysis of the compound No. 68 agreed very closely with the calculated values.

|  | C | H | N | Br |
|---|---|---|---|---|
| Calculated (%) | 60.9 | 3.9 | 4.2 | 23.8 |
| Found (%) | 60.8 | 4.1 | 4.1 | 23.6 |

EXAMPLE A

Three parts of the compound No. 3 as an electron-donating color former was dissolved in 100 parts of 1,1-diphenylethane at 100° C. Separately, an encapsulating material-containing liquor was prepared by dissolving 25 parts of pigskin gelatin (isoelectric point 8) and 25 parts of gum arabic in 300 parts of warm water of 50° C.

The color former-containing oil prepared above was dispersed in the liquor while stirring to form an emulsion. The emulsion was further diluted with 1,000 parts of warm water and adjusted to 4 to 4.3 of pH by the gradual addition of acetic acid, whereby the encapsulating materials were deposited around the individual oil droplets in the emulsion to form a sol of colloid capsules. The capsules were gelled by cooling down to about 10° C and then hardened by the addition of 10 parts of 25% aqueous glutaraldehyde.

The capsule-containing coating liquor thus prepared was applied onto one side of 45 g/m² paper in an amount of 5 g/m² on dry basis to form a color former capsule-coated layer.

On the other hand, an electron acceptor-containing coating liquor was prepared by dispersing 100 parts of acid clay as an electron-acceptor in 200 parts of water and then by adding thereto 30 parts of a styrenebutadiene latex (solid content 50%). The coating liquor thus obtained was applied onto the other side of the paper in an amount of 5 g/m² on dry basis to form an electron acceptor-coated layer.

Several sheets of pressure-sensitive copying paper thus obtained were laid one upon another so that the different layers faced each other, and impressed with a pencil or the like to produce brilliant greenish black copied images on the electron acceptor-coated surfaces. The copied images had a good thermal stability and did not change in color nor disappear even when brought into contact with water or alcohol, or exposed to light.

Thus, it was found that the pressure-sensitive copying paper thus obtained had good performances including good light fastness.

EXAMPLE B

Pressure-sensitive copying paper was prepared in the same manner as described in Example A, except that the fluoran compound No. 12 was used as an electron-donating color former. Copied image obtained on electron acceptor-coated surface gave a pure black color which had good resistance to heat and did not change in color even when exposed to light or brought into contact with water and alcohol.

Thus, a black pressure-sensitive copying paper of high performance was obtained using a single coloring matter.

EXAMPLE C.

Pressure-sensitive copying paper was prepared in the same manner as described in Example A, except that the fluoran compounds No. 4 to No. 11 were used separately as an electron-donating color former. Copied images obtained on electron acceptor-coated surface gave a greenish black color (Nos. 4, 5, 10), a green color (No. 7), a black brown color (Nos. 6, 9, 11) and a black color (No. 8), all of which had the same good fastnesses to light, water and heat as in the case of Example A.

EXAMPLE D

Pressure-sensitive copying paper was prepared in the same manner as described in Example A, except that the fluoran compounds No. 13 to No. 17 were used separately as an electron-donating color former. Copied images obtained on electron acceptor-coated surface gave a black color (Nos. 14, 15, 16, 17) and a reddish black color (No. 13), all of which had the same good fastnesses to light and water as in the case of Example B.

EXAMPLE E

Pressure-sensitive copying paper was prepared in the same manner as described in Example A, except that the fluoran compound No. 19 was used as an electron-donating color former. Copied image obtained on electron acceptor-coated surface gave a violet black color which had the same good fastnesses to light, water and heat as in the case of Example A.

EXAMPLE F

Pressure-sensitive copying paper was prepared in the same manner as described in Example A, except that the fluoran compounds NO. 21 to No. 24 were used separately as an electron-donating color former. Copied images obtained on electron acceptor-coated surface gave a greenish black color on contacting with silica gel, which had the same good fastnesses to light, water and heat as in the case of Example A.

EXAMPLE G

Pressure-sensitive copying paper was prepared in the same manner as described in Example A, except that the fluoran compounds No. 25 to No. 28 were used separately as an electron-donating color former. Copied images obtained on electron acceptor-coated surface gave a green color, which had the same good fastnesses to water, alcohol, light and heat as in the case of Example A.

EXAMPLE H

Pressure-sensitive copying paper was obtained in the same manner as described in Example A, except that the fluoran compounds No. 49 to No. 52 were used separately as a electron-donating color former. Copied images obtained on electron acceptor-coated surface gave a greenish black to black color, which had good fastnesses to water, heat and light.

EXAMPLE I

Pressure-sensitive copying paper was prepared in the same manner as described in Example A, except that the fluoran compounds No. 57 to No. 59 were used separately as an electron-donating color former. Copied images obtained on electron acceptor-coated surface gave a greenish black color, which had good fastnesses to water, heat and light.

EXAMPLE J

Pressure-sensitive copying paper was prepared in the same manner as described in Example A, except that the fluoran compounds No. 61 to No. 67 were used separately as an electron-donating color former. Copied images obtained on electron acceptor-coated surface gave a green to reddish black color, which had good fastnesses to water, heat and light.

EXAMPLE K

Pressure-sensitive copying paper was prepared in the same manner as described in Example A, except that 3 parts of the compound No. 53, 2 parts of 2-tert.-butyl-4-methyl-6-diethylaminofluoran and 1 part of 2-anilino-8-diethylamino-benz[c]fluoran were dissolved, as an electron-donating color former, in 100 parts of 1,1-diphenylethane.

Copied images obtained on electron acceptor-coated surface gave a black color, and maintained the original tone even after a long-term storage.

EXAMPLE L

Pressure-sensitive copying paper which developed a black color was obtained in the same manner as described in Example K, except that the compound No. 53 was replaced by 3 parts of each of the compounds Nos. 18, 24, 27, 28, 54 and 55.

Copied images obtained on electron acceptor-coated surface gave a black color, and maintained the original tone even after a long-term storage.

EXAMPLE M

In 100 parts of olive oil were dissolved at 100° C 2 parts of crystal violet lactone, 3 parts of the compound No. 50 and 3 parts of 2-methylamino-6-diethylaminofluoran which developed a red color on an electron-acceptor.

The color former-containing oil was dispersed in a mixture of 500 parts of a 10% gelatin solution and 500 parts of a 10% gum arabic solution at 60° C to form an emulsion. Then, the emulsion was diluted with 1,000 parts of warm water of 40° C.

A 10% acetic acid solution was gradually added dropwise thereto at 50° C while stirring to adjust the pH to 4 to 4.3 and then the emulsion was further cooled to a temperature below 15° C. At this temperature, 500 parts of a 20% dispersion of titanium dioxide having a particle size of 0.2 to 0.4$\mu$ were gradually added followed by addition of 100 parts of 10% formalin. Further, a 10% caustic soda solution was gradually added dropwise to ajust the pH to 10 to 10.5. The dispersion thus obtained is referred to as "A liquor."

On the other hand, 40 parts of a 10% caustic soda solution and 200 parts of activated clay were dispersed in 400 parts of water, and further 200 parts of 10% polyvinyl alcohol were added thereto. The dispersion thus obtained was uniformly mixed with the abovementioned A liquor to obtain a coating liquor.

The coating liquor was applied onto one side of 40 g/m$^2$ paper in an amount of 7 g/m$^2$ on dry basis and then dried. The resulting pressure-sensitive copying paper is a "self-contained" type one which develops a brilliant black color when pressure is applied onto the coated surface thereof. The developed color did neither change in color nor disappear on exposure to light or moisture.

EXAMPLE N

Pressure-sensitive copying paper which developed a black color on an electron-acceptor was obtained in the same manner as described in Example M, except that the compound No. 50 was replaced by 3 parts of each of the compounds Nos. 49, 51, 57 and 58.

Copied images obtained on electron acceptor-coated surface gave a black color, which did neither change in color nor disappear on exposure to light or moisture.

EXAMPLE O

The capsule-containing coating liquor as prepared in Example A was applied onto one side of 45 g/m$^2$ paper in an amount of 4 g/m$^2$ on dry basis and dried. Further, the electron-acceptor containing liquor as prepared in Example A was applied onto the coated surface in an amount of 4 g/m$^2$ on dry basis and dried. The resulting pressure-sensitive copying paper is a "self-contained"

type one, on one side of which both a color former capsule-coated layer and an electron acceptor-coated layer were formed.

In the present invention, a combined use of electron-acceptors and metals or metal compounds is very effective for promoting the development of image by the reaction between the acceptors and the new fluoran type coloring matters of formula (I), for example, a color depth and developing velocity of image, and in addition fastnesses to light and water. Examples of the useful metals or metal compounds are manganese, nickel, cobalt, iron, zinc, copper, cadmium, mercury, silver and platinum and their compounds.

The same good pressure-sensitive copying paper can also be prepared by replacing the electron acceptor-containing liquor used in Examples A to N by coating liquors of the following recipes:

|  |  | Parts by weight |
|---|---|---|
| (a) | Water | 200 |
|  | Acid clay | 100 |
|  | Cadmium hydroxide | 10 |
|  | Styrene-butadiene latex | 20 |
| (b) | Water | 200 |
|  | Acid clay | 100 |
|  | Manganese acetate | 5 |
|  | Styrene-butadiene latex | 15 |
| (c) | Water | 200 |
|  | Acid clay | 100 |
|  | Copper sulfate | 3 |
|  | Latex | 10 |
| (d) | Water | 200 |
|  | Acid clay | 100 |
|  | Ferrous sulfate | 3 |
|  | Latex | 15 |
| (e) | Water | 200 |
|  | Acid clay | 100 |
|  | Zinc acetate | 10 |
|  | Latex | 20 |
| (f) | Water | 200 |
|  | Acid clay | 100 |
|  | Cobalt sulfate | 5 |
|  | Latex | 15 |
| (g) | Water | 200 |
|  | Acid clay | 100 |
|  | Nickel acetate | 5 |
|  | Latex | 15 |
| (h) | Water | 200 |
|  | Attapulgite | 100 |
|  | Zinc oxide | 5 |
|  | Latex | 15 |

EXAMPLE P

A thermo-responsive (or heat-sensitive) recording material was prepared in the following manner.

Thirty parts of the compound No. 19 as a color former was dispersed, by means of a high shear mixer, in a mixture of 150 parts of a 10% aqueous solution of polyvinyl alcohol and 65 parts of water (Component A). In the same manner as above, 35 parts of Bsiphenol Bisphenal were dispersed in a mixture of 150 parts of the polyvinyl alcohol solution and 65 parts of water (Component B). Three parts of Component A and 67 parts of Component B were combined and coated on the paper sheet in an amount of 5 g/m² on a dry basis. The resulting sheet may be used alone as a copy-receiving sheet, and gives a black copied image on a heat-sensitive copying machine.

EXAMPLE Q

A thermo-responsive (or heat-sensitive) recording material was prepared as follows:

Ten parts of 2-benzoylamino-6-diethylaminofluoran and 30 parts of the compound No. 35 were dispersed, by means of a high shear mixer, in a mixer of 150 parts of a 10% aqueous solution of polyvinyl alcohol and 65 parts of water (Component C). In the same manner as above, 35 parts of 4,4'-dihydroxydiphenyl was dispersed in a mixture of 150 parts of a 10% aqueous solution of polyvinyl alcohol and 65 parts of water (Component D). Three parts of Component C and 67 parts of Component D were combined and coated on the paper sheet in an amount of about 5 g/m² on a dry basis. The resulting may be used alone as a copy-receiving sheet, and gives a black copied image.

What is claimed is:

1. A compound of the formula,

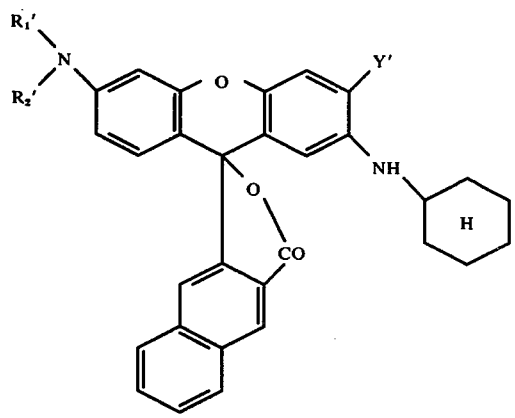

wherein $R_1'$ is methyl, ethyl or cyclohexyl, $R_2'$ is methyl or ethyl and $Y'$ is hydrogen or a lower alkyl.

2. A compound represented by the formula,

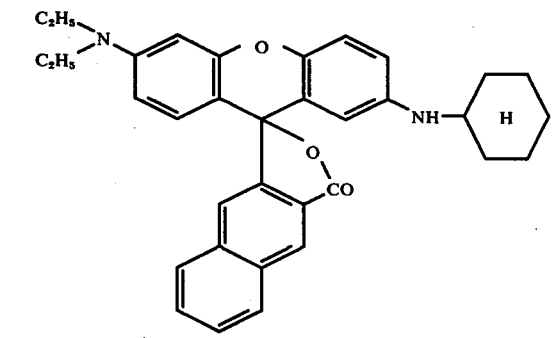

3. A compound represented by the formula,

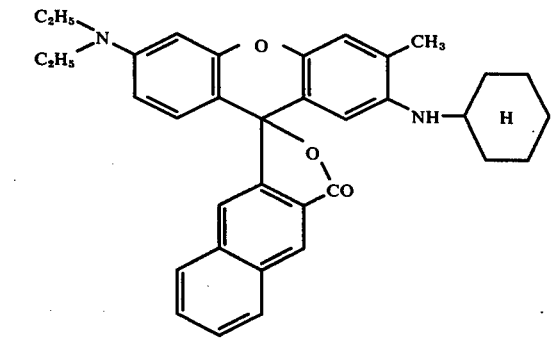

* * * * *